United States Patent [19]

Novak

[11] 4,415,878
[45] Nov. 15, 1983

[54] PARTIAL PRESSURE OF OXYGEN SENSOR-III

[75] Inventor: Robert F. Novak, Farmington Hills, Mich.

[73] Assignee: Ford Motor Company, Dearborn, Mich.

[21] Appl. No.: 429,412

[22] Filed: Sep. 30, 1982

[51] Int. Cl.$^3$ .............................................. H01L 7/00
[52] U.S. Cl. .................................. 338/34; 73/27 R; 422/98
[58] Field of Search .......................... 338/34, 28, 13; 73/27 R; 422/98

[56] References Cited

U.S. PATENT DOCUMENTS 3,933,028 1/1976 Laud et al. ........................ 338/28 X
4,236,138 11/1980 Segawa et al. ................. 73/27 R X

*Primary Examiner*—C. L. Albritton
*Attorney, Agent, or Firm*—William E. Johnson; Olin B. Johnson

[57] ABSTRACT

A partial pressure of oxygen sensor which finds utility when inserted into an exhaust system of a hydrocarbon fuel burning device. The oxygen sensor includes a mounting body both (a) threaded on one end for securement to the exhaust system, and (b) having a cylindrical configured bore extending along a central axis thereof. A heated sensing element of cylindrical configuration is also provided which includes a ceramic support, a resistance heater element wrapped around the ceramic support, and a titania dioxide sensor element closely located to the resistance heater element. The heated sensing element is mounted in the cylindrical configured bore of the mounting body in a manner that the titania dioxide sensor thereof projects beyond a threaded end of the mounting body. A protection device is provided over the titania dioxide sensor to protect the same and to permit exhaust gases to flow thereby. Electrical connections are made at the rear end of the mounting body to the resistance heater element and the titania dioxide sensor. Further structure is provided for supporting and sealing electrical lead wires and providing electrical connections in a manner that the heating element is connected to a source of voltage and the sensing element to a sensing circuit.

5 Claims, 8 Drawing Figures

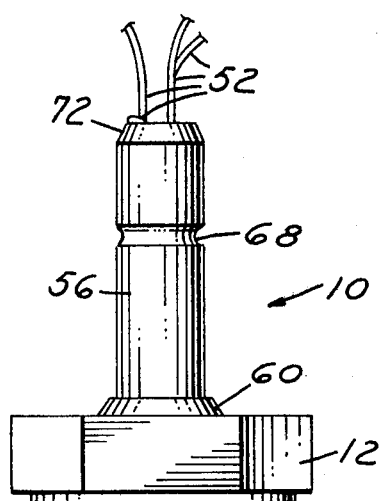
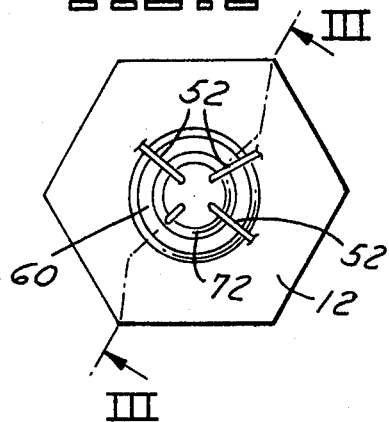
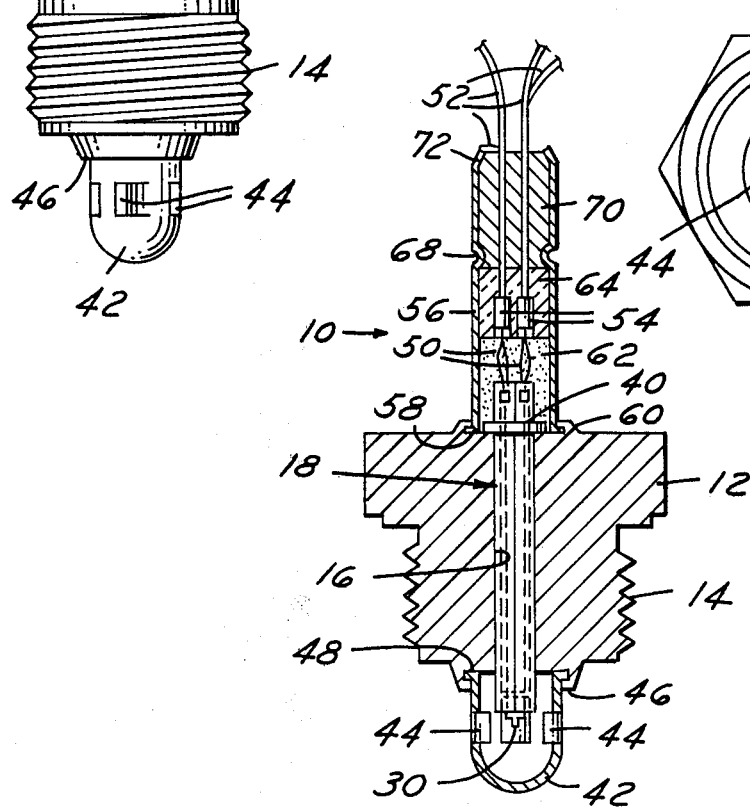
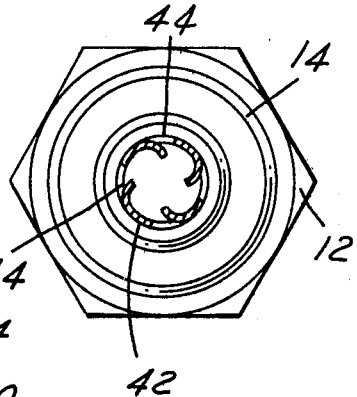

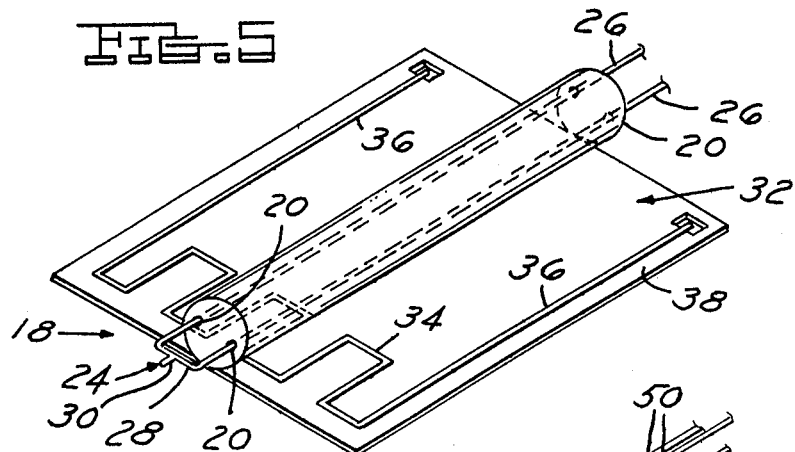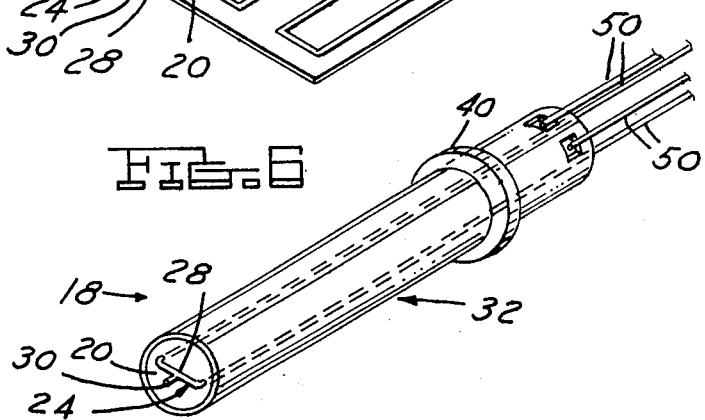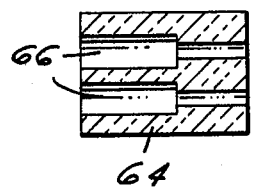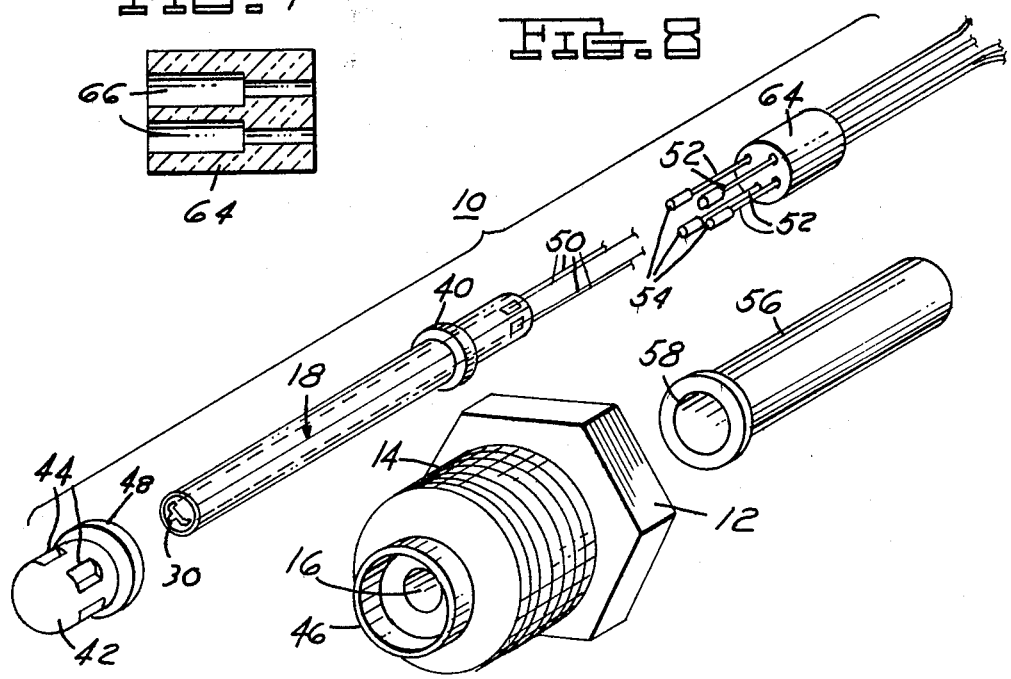

PARTIAL PRESSURE OF OXYGEN SENSOR-III

BACKGROUND ART AND PRIOR ART STATEMENT

The present invention is directed to the field of devices for controlling a hydrocarbon fuel burning device. In particular, the present invention is directed to a partial pressure of oxygen sensor which is inserted into an exhaust system which carries the exhaust gases from a hydrocarbon fuel burning device. The partial pressure of oxygen sensor is used with appropriate circuitry and mechanical devices associated therewith for controlling the amount of fuel which is introduced into the hydrocarbon fuel burning device. The amount of fuel being introduced into the device is a function of the amount of oxygen detected by the partial pressure of oxygen sensor in the exhaust gases flowing through the exhaust system.

Ceramic exhaust gas sensors of the electrically variable resistance type are known. For example, commonly assigned U.S. Pat. 3,893,230 by H. L. Stadler et al describes one such sensor fabricated from titania ceramic material. Also, commonly assigned U.S. Pat. 3,933,028 described such a sensor fabricated from cobalt monoxide ceramic material. Each of these sensor materials demonstrates an electrical resistance change as a function of the partial pressure of oxygen in the gaseous environment of the ceramic material when that material is located in the exhaust system of a hydrocarbon fuel burning device. The resistance changes may be measured by suitable electrodes. Each of the named sensing materials function best at an elevated temperature.

The present invention is directed to a particular structure for forming a partial pressure of oxygen sensor. The particular structure is one which provides a sensor of rugged construction, yet one which is efficient and effective in operation.

DISCLOSURE OF THE INVENTION

This invention is directed to a partial pressure of oxygen sensor and, more particularly, to a partial pressure of oxygen sensor for insertion into an exhaust system of a hydrocarbon fuel burning device.

In accordance with the teachings of this invention, the partial pressure of oxygen sensor comprises the following combination. A mounting body is formed of a metallic material. This mounting body is threaded on one end so that it may be secured to the exhaust system of the hydrocarbon fuel burning device. The mounting body has a cylindrical configured bore of a first diameter extending along a central axis thereof.

The combination includes a heated sensing element which is constructed in the following manner. A ceramic support of generally circular cross section is provided which has a pair of openings extending therethrough. A sensing element supporting wire has (a) a pair of leg portions extending through the pair of openings of the ceramic support, and (b) a support portion intermediate the leg portions thereof in juxtaposition to a free end of the ceramic support. A titania dioxide sensing element is mounted upon the support portion of the sensing element supporting wire. A resistance heater element is wrapped around the ceramic portion. The resistance heater element heats the sensing element to a required temperature when a preselected voltage is applied across the resistance heater element. A locating ring is bonded to a rear portion of the heated sensing element. The heated sensing element has a diameter slightly less than the first diameter of the cylindrical configured bore of the mounting body so that the heated sensing element may be received within the cylindrical configured bore. The locating ring of the heated sensing element locates the heated sensing element in the bore in a manner such that the titania dioxide sensing element thereof extends beyond the cylindrical bore of the threaded end of the mounting body.

A first protection tube, having an opening therein is secured to the threaded end of the mounting body. This first protection tube provides protection for the titania dioxide heating element. The opening of the first protection tube permits exhaust gases to pass through the protection tube and come into contact with the titania dioxide sensing element.

The combination includes a plurality of fine electrical lead lines. A pair of the fine lead lines is bonded to and extends from opposite ends of the resistance heater element. A pair of the fine lead lines is also bonded to and extends from opposite ends of the sensing element supporting wire. A plurality of electrical lead lines are also provided which are equal in number to the fine electrical lead lines. A plurality of crimped bands are also employed. Each of the crimped bands interconnects paired ones of the electrical lead lines and the fine electrical lead lines.

The combination also includes a ceramic insulator body which has a plurality of passageways therein equal in number to the plurality of crimped bands. The passageways are so constructed and arranged that each of the passageways has an associated pair of the interconnected lead lines passing therethrough. Each of the crimped bands interconnecting the lead lines come into locating engagement with the side walls defining the associated passageways in order to locate the interconnected leads positively within the passageway.

A second protection tube has one end thereof secured to an end of the mounting body not having the threads thereon. The second protection tube encloses and protects the ceramic insulator body and the elements which are received within and pass therethrough.

A ceramic cement occupies a volume between the ceramic insulator body and a rear portion of the heated sensing element received in the cylindrical configured bore of the mounting body. A high temperature resistant sealant material occupies a volume between the ceramic insulator body and a free end of the second protection tube. An electrical terminal is connected to the plurality of electrical lead lines for independently connecting the lead lines from the resistance heater element to a source of voltage and from the titania dioxide sensing element to a sensing circuit.

BRIEF DESCRIPTION OF THE DRAWINGS

The novel features that are considered characteristic of the invention are set forth with particularity in the appended claims. The invention itself, however, both as to its organization and its method of operation, together with additional objects and advantages thereof, will best be understood from the following description of specific embodiments when read in conjunction with the accompanying drawings, wherein like reference characters indicate like parts throughout the several figures, and in which:

FIG. 1 is an elevation view of an assembled partial pressure of oxygen sensor in accordance with the teachings of this invention;

FIG. 2 is a plan view of the oxygen sensor of FIG. 1;

FIG. 3 is an elevation view taken along line III—III of FIG. 2 showing a cross section of the oxygen sensor of this invention;

FIG. 4 is a bottom view of the sensor of FIG. 1;

FIG. 5 is a perspective view of a heated sensing element prior to complete assembly thereof;

FIG. 6 is a perspective view of the heated sensing element of FIG. 5 after complete assembly thereof;

FIG. 7 is a cross section view of an insulator body used in the structure of this invention; and FIG. 8 is a schematic view of various elements making up the oxygen sensor of this invention prior to assembly of the structure.

BEST MODE AND INDUSTRIAL APPLICABILITY

The following description is what I consider to be a preferred embodiment of my partial pressure of oxygen sensor. The following description also sets forth what I now contemplate to be the best mode of building this oxygen sensor. This description is not intended to be a limitation upon the broader principles of this oxygen sensor and while preferred materials are used to illustrate the oxygen sensor in accordance with the requirements of the patent laws it does not mean that the oxygen sensor can be constructed only with the stated materials as others may be substituted therefor.

In accordance with the teachings of a preferred embodiment of this invention, a partial pressure of oxygen sensor, generally identified by the numeral 10, is shown in the drawings. The oxygen sensor is made up of a plurality of elements for forming the total combination. The plurality of elements will be described in greater detail hereinbelow. As is well known to those skilled in the art, the oxygen sensor is designed for insertion into an exhaust system of a hydrocarbon fuel burning device. The oxygen sensor serves as a device for sensing the amount of oxygen in the exhaust gases. The oxygen sensing device produces a variable resistance in repsonse to the amount of oxygen in the ambient surrounding the same, the resistance being an indication of the partial pressure of oxygen. The signal generated by the oxygen sensor is then fed to associated circuitry which uses the same to set an air/fuel metering device, such as a carburetor, to obtain a desired stoichiometric relationship between the air coming into the fuel burning device and the amount of fuel being burned. All of this type of operation is well known to a skilled artisan.

A first portion of the oxygen sensor 10 is a mounting body 12. The mounting body is formed of a metallic material and has a threaded portion 14 on one end thereof. The threaded portion is used for securing the oxygen sensor to the exhaust system of the hydrocarbon fuel burning device.

As is seen in FIGS. 3 and 8, the mounting body 12 has a cylindrical configured bore 16 extending along a central axis thereof. The cylindrical configured bore is for a purpose which will be described in greater detail hereinbelow.

An elongated, heated sensing element, generally identified by the number 18 (best seen in FIGS. 5 and 6), forms another element of the oxygen sensor 10. As is best seen in FIG. 5, the heated sensing element 18 includes a ceramic support 20 of generally circular cross section having a pair of openings 22—22 extending therethrough. A sensing element supporting wire, generally identified by the numeral 24, has a pair of leg portions 26—26 extending through the pair of openings 22—22 of the ceramic support 20. The sensing element support wire 24 also has a support portion 28 intermediate the leg portions 26—26 thereof, which support portion is in juxtaposition to a free end of the ceramic support 20. A titania dioxide sensing element 30 is mounted upon the support portion 28 of the sensing element support wire 24 in a manner which is described more thoroughly in a commonly assigned copending application entitled "Method of Making a Titania Dioxide Sensor Element-II", identified by Ser. No. 429,413, filed on even date herewith.

Another portion of the heated sensing element 18 is a resistance heating element, generally identified by the numeral 32. FIG. 5 shows this particular element in its unassembled condition and FIG. 6 shows this element in its assembled condition. In order to form this resistance heating element 32, a resistance heater 34 and terminal legs 36—36 are silk screen printed on a layer of ceramic material 38, such as alumina. The layer of ceramic material 38 is then wrapped around the ceramic support 20 to form a complete assembly which is then sintered to form a monolithic part which has been previously designated as the heated sensing element 18. The resistance heater element 32 heats the titania dioxide element 30 to a required temperature when a preselected voltage is applied across the resistance heater element so that the sensing element may carry out its intended function.

The heated sensing element 18 has a diameter slightly less than the diameter of the cylindrical configured bore 16 of the mounting body 12. Also, the resistance heating element has a locating ring 40 bonded to a rear portion thereof, as is best seen in FIG. 6. With this construction, when the heated sensing element is received within the cylindrical configured bore 16 of the mounting body 12, the locating ring 40 will locate the heated sensing element so that the titania dioxide sensing element 30 will extend beyond the cylindrical bore of the mounting body, as is best seen in FIG. 3.

A first protection tube 42 having a plurality of openings 44—44 therein is bonded to the lower end of the threaded portion 14 of the mounting body 12, as may best be seen in FIG. 3. A lip portion 46 of the mounting body 12 is folded over a lip portion 48 of the first protection tube 42 in order to join the two elements together.

A plurality of fine electrical lead lines 50—50 are used to make electrical contact to the resistance heater element 32 and the titania dioxide sensing element 30. Fine electrical lead lines are bonded to the terminal legs 36—36 of the resistance heater 34 on the layer of ceramic material 38. In a similar manner an electrical lead line is bonded to and extends from each of the leg portions 26—26 of the sensing element support wire 24 upon which the titania dioxide sensing element 30 is bonded.

As will best be understood by reference to FIGS. 3 and 8, a plurality of electrical lead lines 52—52 are also provided which are equal in number to the number of fine electrical lead lines 50—50. A plurality of crimped bands 54—54 are independently used for interconnecting paired ones of the fine electrical lead lines 50—50 and the electrical lead lines 52—52. Paired lead lines are inserted within the band, and the band 54 is then crimped in order to secure the lead lines therewithin.

In the normal assembly operation the heated sensing element would be dropped into the cylindrical configured bore 16 of the mounting body 12 until the locating ring 40 comes into contact with the rear end of the bore, as is best seen in FIG. 3. In this condition the titania dioxide sensing element 30 is located and protected within the first protection tube 42, but is exposed to exhaust gases by means of the openings 44—44 in that tube.

A second protection tube 56 (best seen in FIGS. 3 and 8) has a lip portion 58 by which it is sealed by means of a lip portion 60 to an end of the mounting body 12 not having the threaded portion 14 thereon.

A ceramic cement 62 (FIG. 3, only) is provided between the upper portion of the heated sensing element 18 and a ceramic insulator body 64. As best seen in FIG. 7, the ceramic insulator body 64 has a plurality of stepped passageways 66—66 passing therethrough. These passageways are so constructed and arranged that each of the passageways will have an associated pair of interconnected leads passing therethrough with the crimped band 54 interconnecting the leads coming into locating engagement with the stepped side walls defining the passageways. This helps to support any load which may be placed on the wires by applying pressure to the electrical leads 52—52.

As previously stated, the ceramic cement 62 is introduced into the second protection tube 56 at a position above the heated sensing element 18. While the cement is still wet, the second ceramic insulator body 64 is threaded onto electrical lead lines 52—52 and thereafter introduced through the top of the second protection tube and forced against the ceramic cement. Thereafter, the second protection tube is crimped at crimp 68 to hold the second ceramic insulator body in place.

After the crimping operation and after the ceramic cement 62 has been allowed to cure, the remainder of the second protection tube 56 is filled with a high temperature resistant sealant material 70, seen only in FIG. 3. The high temperature sealant material occupies a volume between the ceramic insulator body 64 and a free end of the second protection tube 56. A preferred high temperature resistant sealant material can be, for example, a silicone RTV material suitable for high temperature environments; that is, environments heated to a temperature above 300° C. This sealant material will seal the top of the oxygen sensor 10 against moisture and salt spray. As is best seen in FIGS. 1 and 3, a free end 72 of the second protection tube 56 is crimped around the high temperature sealant material to complete the sealing of the oxygen sensor.

The electrical lead lines 52—52 extending from the free end 72 of the second protection tube 56 may be secured to any suitable electrical connector (not shown) so that those leads may be properly connected to required circuitry. For example, the electrical leads 52—52 associated with the resistance heating element 32 should be connected to a source of voltage so that the heating circuit can be actuated to heat the oxygen sensor 10. In a similar manner the electrical lead lines 53—52 associated with the sensing element support wire 24 supporting the titania dioxide sensing element 30 should be connected by means of the suitable connector to a sensing circuit. In this manner the output of the titania dioxide element may be applied to suitable circuitry, whereby other mechanical portions of the hydrocarbon fuel burning device may be controlled so that the proper amounts of oxygen and fuel are being used in the system.

While a preferred embodiment of the invention has been illustrated and described, it will be obvious to those skilled in the art that various changes and modifications may be made without departing from the invention, and it is intended to cover in the appended claims all such modifications and equivalents as fall within the true spirit and scope of this invention.

I claim:

1. A partial pressure of oxygen sensor for insertion into an exhaust system of a hydrocarbon fuel burning device, comprising in combination:

a mounting body formed of a metallic material threaded on one end for securement to the exhaust system and having a cylindrical configured bore of a first diameter extending along a central axis thereof;

a heated sensing element including: a ceramic support of generally circular cross section having a pair of openings extending therethrough, a sensing element supporting wire having (a) a pair of leg portions extending through said pair of openings of said ceramic support, and (b) a support portion intermediate said leg portions thereof in juxtaposition to a free end of said ceramic support, a titania dioxide sensing element mounted upon said support portion of said sensing element supporting wire, a resistance heater element wrapped around said ceramic support so that said resistance heater element heats said sensing element to a required temperature when a preselected voltage is applied across said resistance heater element, and a locating ring bonded to a rear portion of said heated sensing element, said heated sensing element having a diameter slightly less than said first diameter of said cylindrical configured bore of said mounting body so that said heated sensing element may be received within said cylindrical configured bore with said locating ring locating said heated sensing element in a manner such that said titania dioxide sensing element thereof extends beyond said cylindrical bore of said threaded end of said mounting body;

a first protection tube secured to said threaded end of said mounting body for protecting said titania dioxide heating element, said first protection tube having openings therein for permitting exhaust gases to pass therethrough and come into contact with said titania dioxide sensing element;

a plurality of fine electrical lead lines, a pair of said fine lead lines being bonded to and extending from said resistance heater element and a pair of said fine lead lines being bonded to and extending from said sensing element supporting wire;

a plurality of electrical lead lines equal in number to said fine electrical lead lines;

a plurality of crimped bands, each of said crimped bands for interconnecting paired ones of said electrical lead lines and said fine electrical lead lines;

a ceramic insulator body having a plurality of passageways therein equal in number to said plurality of said crimped bands, said passageways being so constructed and arranged that each of said passageways have an associated pair of said interconnected leads passing therethrough with said crimped band interconnecting the same coming into locating engagement with the side walls defining said associated passageway;

a second protection tube means having one end secured to an end of said mounting body not having said threads thereon for enclosing and protecting said ceramic insulator body and elements received therein and passing therethrough;

a ceramic cement occupying a volume between said ceramic insulator body and a rear portion of said heated sensing element received in said cylindrical configured bore of said mounting body;

a high temperature resistant sealant material occupying a volume between said ceramic insulator body and a free end of said second protection tube means; and electrical terminal means connected to said plurality of electrical lead lines for independently connecting said lead lines as required to a source of voltage and to a sensing current.

2. The partial pressure of oxygen sensor as defined in claim 1, wherein each of said passageways of said second ceramic insulator body are of a stepped design in which a first portion of each passageway has a diameter greater than an associated one of said crimped bands received therein and a second portion of each passageway has a diameter less than an associated one of said crimped bands but greater than an associated one of said electrical lead lines passing therethrough.

3. The partial pressure of oxygen sensor as defined in claim 1 or claim 2, wherein said first protection tube has a plurality of openings therein.

4. The partial pressure of oxygen sensor as defined in claim 1, wherein each of said passageways of said second ceramic insulator body are of a tapered design in which a front face of each passageway has a diameter greater than an associated one of said crimped bands received therein and a back face of each passageway has a diameter less than an associated one of said crimped bands but greater than an associated one of said electrical lead lines passing therethrough.

5. The partial pressure of oxygen sensor as defined in claim 1 or claim 4, wherein said first protection tube has a plurality of openings therein.

* * * * *